United States Patent
Ochiai et al.

(10) Patent No.: US 6,765,205 B2
(45) Date of Patent: Jul. 20, 2004

(54) ELECTRON MICROSCOPE INCLUDING APPARATUS FOR X-RAY ANALYSIS AND METHOD OF ANALYZING SPECIMENS USING SAME

(75) Inventors: Isao Ochiai, Otsuki (JP); Toshiei Kurosaki, Hitachinaka (JP); Toshiro Kubo, Hitachinaka (JP); Naomasa Suzuki, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 10/601,531

(22) Filed: Jun. 24, 2003

(65) Prior Publication Data

US 2004/0099805 A1 May 27, 2004

(30) Foreign Application Priority Data

Nov. 1, 2002 (JP) ........................ 2002-319247

(51) Int. Cl.[7] ...................... G01N 23/00; G21N 23/225
(52) U.S. Cl. ...................... 250/310; 250/305; 250/309; 250/310; 250/492.1; 250/492.21; 378/44; 378/45; 378/49; 356/237.4
(58) Field of Search ...................... 378/44, 45, 46, 378/48, 49; 356/237.4; 250/492.1, 491.21, 492.2, 397, 398, 305, 306, 307, 309, 310, 311, 308

(56) References Cited

U.S. PATENT DOCUMENTS

| | | | | |
|---|---|---|---|---|
| 4,288,692 A | * | 9/1981 | Schamber et al. | 250/310 |
| 4,476,386 A | * | 10/1984 | Reid et al. | 250/310 |
| 4,712,057 A | * | 12/1987 | Pau | 250/310 |
| 5,299,138 A | * | 3/1994 | Fiori et al. | 702/22 |
| 5,362,964 A | * | 11/1994 | Knowles et al. | 250/310 |
| 5,550,372 A | * | 8/1996 | Yasue | 250/310 |
| 5,898,179 A | * | 4/1999 | Smick et al. | 250/492.21 |
| 6,140,643 A | * | 10/2000 | Brown et al. | 250/307 |
| 6,268,609 B1 | * | 7/2001 | Ryding et al. | 250/492.21 |
| 6,271,530 B1 | * | 8/2001 | Smick et al. | 250/492.21 |
| 6,292,532 B1 | * | 9/2001 | Kawahara et al. | 378/49 |
| 6,441,897 B1 | * | 8/2002 | Zeimantz | 356/237.4 |
| 6,603,119 B1 | * | 8/2003 | Giannuzzi et al. | 250/229 |

FOREIGN PATENT DOCUMENTS

| | | | |
|---|---|---|---|
| JP | 63-108253 | 5/1988 | ........ G01N/23/225 |
| JP | 8-148111 | 6/1996 | ........ H01J/37/244 |
| JP | 2000-321225 | 11/2000 | ........ G01N/23/225 |
| JP | 2001-68518 | 3/2001 | ........ H01L/21/66 |

* cited by examiner

Primary Examiner—John R. Lee
Assistant Examiner—David A. Vanore
(74) Attorney, Agent, or Firm—Antonelli, Terry, Stout & Kraus, LLP

(57) ABSTRACT

An electron microscope including an apparatus for x-ray analysis, is capable of performing elemental analysis with X-rays emitted from a specimen by electron beam irradiation, that is, inspection of foreign particles, for enhancement of yields in manufacturing, at high speed and with high precision and high space resolving power. The current quantity of the electron beam is automatically controlled such that an X-ray count rate falls within a range of 1000 to 2000 counts per second, a plurality of X-ray energy regions are set up when checking an X-ray spectrum against reference spectra stored in a database for analysis of the X-ray spectrum, matching is performed for each of the X-ray energy regions, and the distribution of the elements observed is analyzed on the basis of an intensity ratio between X-ray sample spectra obtained by electron beam irradiation at not less than two varied acceleration voltages.

2 Claims, 13 Drawing Sheets

WAFER CARRIER

FIG.8

| ROI NUMBER | ENERGY REGION | | RESULT | | IN ORDER OF THE DEGREE OF MATCHING | | |
|---|---|---|---|---|---|---|---|
| | | | | | BEST | 2ND | 3RD |
| #1 | START | 0.2 | DEGREE OF MATCHING $x^2$ | | 1.5 | 25 | 205 |
| | END | 0.7 | HIGHT PARAMETER (RATIO OF COUNT) | | 0.05 | 0.012 | 0.0001 |
| | | | NAME OF MATTER (SPECTRUM LABEL) | | TiN50nm/Si | Ti50nm/Si | SiO2 |
| #2 | START | 1.5 | DEGREE OF MATCHING $x^2$ | | 0.3 | 11.4 | 35 |
| | END | 1.9 | HIGHT PARAMETER (RATIO OF COUNT) | | 0.11 | 0.15 | 0.09 |
| | | | NAME OF MATTER (SPECTRUM LABEL) | | Si | Ta | W |
| FULL | START | 0.2 | DEGREE OF MATCHING $x^2$ | | 1.2 | 1.5 | 1.6 |
| | END | 5.0 | HIGHT PARAMETER (RATIO OF COUNT) | | 0.1 | 0.15 | 0.12 |
| | | | NAME OF MATTER (SPECTRUM LABEL) | | TiN50nm/Si | Ti50nm/Si | Si |

FIG.21A    FIG.21B
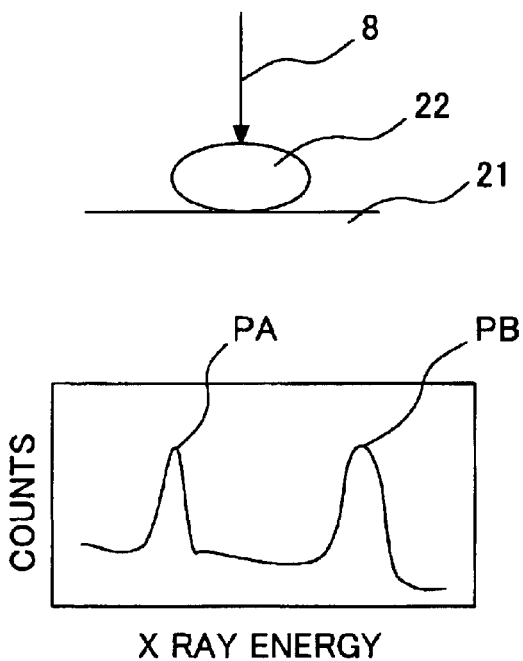
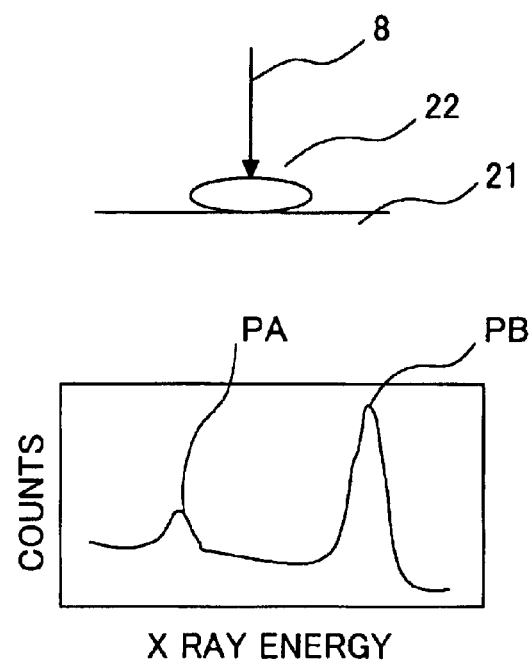
FIG.22
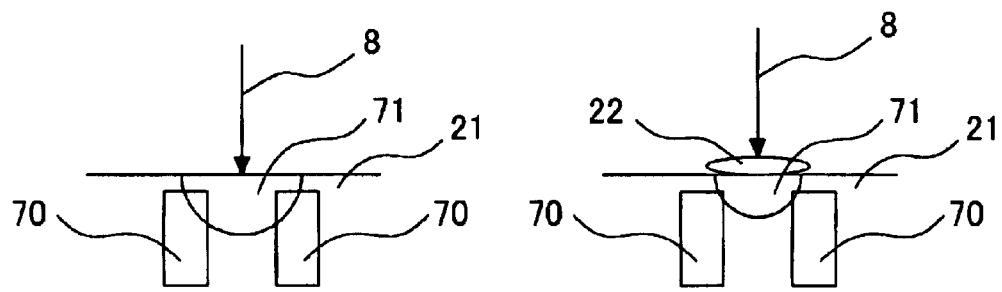

ELECTRON MICROSCOPE INCLUDING APPARATUS FOR X-RAY ANALYSIS AND METHOD OF ANALYZING SPECIMENS USING SAME

BACKGROUND OF THE INVENTION

The present invention relates to an instrument system, including an electron microscope, for use in observation, analysis, and evaluation in the course of research/development and manufacture of electronic devices and micro-devices, such as a semiconductor device, liquid crystal device, and magnetic head.

In the case of manufacturing devices, such as a semiconductor memory, there are situations where foreign particles generated in the course of the manufacturing process are mixed therein. Examples of the foreign particles include foreign species particles attributable to process material represented by the residue of etching operations and the residue of a resist, the wall material of process vessels, the material for fixedly holding a wafer, and the material used for a vacuum gas line, etc. Adhesion of such foreign particles to a wafer results in the generation of defective items at times.

It is important from the viewpoint of improving the yield in the manufacture of various devices to analyze the respective elemental composition of the foreign particles that have adhered to a wafer, and to search for the sources of the foreign particles on the basis of their kinds, thereby removing the causes of generation thereof.

As means for obtaining information on the elemental compositions of specimens, there is a known technique of irradiating the specimen with an electron beam, thereby detecting X-rays that are generated. The X-rays comprise a characteristic X-ray emitted when electrons of atoms on the surface of, and in the vicinity of the surface of, specimens fall from an excited state into a lower energy state, and a continuous X-ray at an energy level below the energy of an incident electron beam due to braking radiation, whereby incident electrons are braked before emission. The characteristic X-ray has energy inherent to respective elements, indicated by K, L, and M lines, respectively, depending on the excited state of the characteristic X-ray. Accordingly, the elemental composition of specimens can be found by analyzing the energy at peaks appearing in a spectrum. This method is called energy dispersive X-ray spectroscopy (EDX or EDS). Instruments for performing this method, supplied by companies such as Oxford Instrument, EDAX, TermoNORAN Instrument, and so forth, are available on the market, and they are capable of providing both qualitative analysis and quantitative analysis. Users can find the elemental composition of specimens by analyzing obtained spectra by means of qualitative analysis and quantitative analysis, respectively.

Another example of a method of identifying the elemental composition of specimens from X-ray spectra is disclosed in JP-A No. 108253/1988 (example 1). This publication describes a method in which respective characteristic X-ray spectra (reference spectra) of a plurality of known substances are registered in a memory, and by checking the X-ray spectrum of an unknown substance against the reference spectra registered in the memory, the unknown substance is identified.

An example of the inspecting of foreign particles on the surface of a wafer by use of the method described is disclosed in JP-A No.14811/1996 (example 2). In this example, there is a configuration wherein the locations of foreign particles are determined by observation of images dependent on the magnitude of reflection electron signals, and, by checking the X-ray spectra of the foreign particles against reference spectra, the elemental compositions of the foreign particles can be identified.

Still another method is disclosed in JP-A No. 321225/2000 (example 3). This publication describes a method wherein the net X-ray spectrum of a foreign particle is found on the basis of an X-ray spectrum of a portion of the surface of a wafer having the foreign particle, and an X-ray spectrum of the rest of the surface of the wafer having no foreign particle, (background spectrum), and the elemental composition of the foreign particle is found by checking the net X-ray spectrum of the foreign particle against a database.

Further, JP-A No. 68518/2001 discloses a method of generalizing information on foreign particles, found by the method described above, and registering the same into predetermined categories, thereby specifying causes of defects.

An electron beam, even if focused in a narrow region, is subjected to interaction with the substance inside a specimen upon impacting on the specimen, thereby undergoing scattering. The magnitude of a scattering region is dependent on the element which serves as the constituent of the specimen and the acceleration voltage of the electron beam. FIGS. 18A through 18D are views of the results of a calculation using a Monte Carlo method, showing electron beam scattering conditions when electron beams with acceleration voltage at 15 kV and 5 kV, respectively, are irradiated to specimens of silicon (Si) and tungsten (W), respectively. In the case of the specimen being silicon, the magnitude of a scattering region of the electron beam is about 4 $\mu$m, if the acceleration voltage is 15 kV, and it is about 0.4 $\mu$m, if the acceleration voltage is 5 kV. Due to the excitation of the electron beams, X-rays are generated substantially in these regions, respectively. This means that the X-ray spectra as observed reflect information on not only the irradiation points of the electron beams, but also the substances contained in the respective scattering regions. Accordingly, the space resolving power in elemental analysis is determined not by the size of an electron beam, but by the magnitude of the scattering region.

Since the processing sizes of semiconductor elements that have attained miniaturization have lately reached sub-micron levels, the sizes of foreign particles causing degradation in the characteristics of the elements have also become smaller. FIG. 19 is a view showing a semiconductor device structure as it appears during a manufacturing process, having respective scattering regions of the electron beams, inside the Si, as shown in FIGS. 18A and 18B. In the case of EDX analysis of a small foreign particle, an electron beam passes through the foreign particle and scatters inside the substrate. Accordingly, an X-ray spectrum as observed contains information on both the foreign particle and the substrate (background), causing difficulty with the analysis. For a substrate in the middle of a manufacturing process, in particular, patterns, that is, an oxide film, electrodes, a dielectric film, and so forth, are formed on the substrate; and, in a case where flakes from those substances constitute foreign particles, the foreign particles need to be distinguished from those substances.

Further, if the acceleration voltage is lowered in order to reduce the effect of the background, that is, to reduce the size of the scattering region, the characteristic X-rays that can be excited are restricted, in which case, elements need to be identified with overlapping characteristic X-ray peaks. Such an instance will be described with reference to FIG. 20. FIG. 20 is a graph showing X-ray spectra of a titanium (Ti) foreign particle 50 nm thick, that is present on the surface of a silicon wafer. The X-ray spectra were obtained by two electron beams having an acceleration voltage of 15 kV and 5 kV, respectively. In the case of the acceleration voltage at 15 kV, a Ti-K line peak is observed at 4.51 keV of X-ray energy; however, in the case of the acceleration voltage at 5 kV, such a peak is not observed because such a characteristic X-ray cannot be excited. In this case, the presence of a titanium element is determined by a Ti-L line that is observed at 0.45 keV of X-ray energy. However, since there exist K-line peaks of oxygen and nitrogen, respectively, in this region of X-ray energy, the characteristic X-ray peaks are observed in an overlapped state, if those elements are present, causing difficulty with the analysis.

Further, in the case of lowering the acceleration voltage, the quantity of X-rays being generated decreases, although the current is sufficient for observation of secondary electron images. For example, in the above-described instance, if the setting of the acceleration voltage only is changed from 15 kV to 5 kV, the quantity of X-rays having the Ti-L line peak is one tenth of the quantity of X-rays having the Ti-K line peak, at the acceleration voltage of 15 kV, which is mainly used for identification of the Ti element, thereby causing a problem of degradation of the accuracy in the identification of elements.

Furthermore, the following problems have been encountered with the conventional methods described in the foregoing.

Analysis by software for qualitative analysis and quantitative analysis, for use with X-ray detectors available in the market, relies on a manual, which is too complicated to be used by a lay person, and is insufficient for controlling the process steps, so that there has been a demand for a system that is capable of automatically outputting an elemental composition.

The methods according to the above-referenced examples 1 and 2 are effective in the case of specimens of a uniform elemental composition, however, in the case where there is a small foreign particle on a substrate, there has been a problem in that, even with foreign particles of an identical elemental composition, the X-ray spectra thereof largely differ from each other, depending on the size (thickness) of the foreign particles, as shown in FIGS. 21A and 21B, resulting in a failure to obtain a match with the reference spectra stored in the database. Although it is conceivable to prepare X-ray spectra corresponding to various thicknesses of foreign particles, this has caused a problem of requiring a longer checking time because of the increase in the number of reference spectra. Further, since the sensitivity (spectral sensitivity) against X-ray energy generally varies on a case-by-case basis due to variations in performance of X-ray detectors and the difference between optical systems for detection, there is a need for preparing X-ray spectra to be provided as a database for every instrument. Furthermore, the spectral sensitivity undergoes a change over time due to stains etc. on an X-ray window, at times causing a problem with the checking of an X-ray spectrum.

The method according to the above-referenced example 3 is a method wherein the net X-ray spectrum of a foreign particle is found on the basis of the X-ray spectrum of the portion of the surface of the wafer, having the foreign particle, and the X-ray spectrum of the rest of the surface of the wafer, having no foreign particle, (the background spectrum), and the elemental composition of the foreign particle is found by checking the net X-ray spectrum of the foreign particle against the data base. In this case, there has been encountered a problem in that there is a possibility that erroneous results will be obtained because components of the X-ray spectrum from the background vary depending on the size of the foreign particle, that is, this is not a case of a simple linear sum of the background spectrum and the X-ray spectrum of the foreign particle portion.

The above-mentioned problem will be described by way of example with reference to FIG. 22. The left part of FIG. 22 is a schematic representation showing a case where an electron beam 8 is irradiated to a silicon wafer 20 incorporating body structures 70 made of an element A. The electron beam 8 scatters in a region 71 that is hemispherical in shape inside the silicon wafer 20; and, in the case where the body structures 70 are present within the region 71, an X-ray spectrum, as observed, comprises the characteristic X-ray peak of silicon and that of the element A. Meanwhile, the right hand part of FIG. 22 is a schematic representation showing a case where a foreign particle 22 made of the element A is present on the surface of the same silicon wafer. The scattering region of an electron beam 8 will be a region 71 that is smaller than the region shown in the left hand figure due to the presence of the foreign particle 22. An X-ray spectrum, as observed in this case, also has the characteristic X-ray peak of silicon and that of the element A. There are cases where the X-ray spectrum obtained in the case of the right hand Figure becomes substantially the same as that in the case of the left hand figure, in which case there has occurred a problem in that the peaks will disappear upon subtracting the X-ray spectrum obtained in the case of the right figure from the X-ray spectrum obtained in the case of the left figure, representing the background.

SUMMARY OF THE INVENTION

In view of the problems described above, it is an object of the invention to provide an electron microscope, including an apparatus for effecting x-ray analysis, that is capable of analyzing the elemental composition of foreign particles on the surface of a specimen with high space resolving power, high precision, and high throughput, and a method of analyzing specimens using the same.

The foregoing object of the invention can be achieved by adoption of the following features:

(1) An electron microscope according to the invention is characterized in that the current quantity of an electron beam is controlled such that the count-number of X rays from the specimens falls within a range of 1000 to 2000 counts per second.

The electron microscope having an electron beam optical system provided with an electron source and a lens for focusing an electron beam, an optical system controller for controlling the electron beam optical system, a specimen stage on which specimens are to be placed, an electron detector for detecting electrons emitted from the specimens by irradiating the specimens with the electron beam, an X-ray detector for detecting X rays radiated from the specimens, and a processor for processing signals from both the detectors and performing image formation and elemental analysis of the specimens, comprises means for detecting the count-number of X rays per unit time by detecting the X rays with the X-ray detector and for feedback-controlling the current quantity of the electron beam on the basis of the count-number of X rays per unit time. Further, the current quantity of the electron beam is feedback-controlled such that the count-number of X rays from the specimens falls within the range of 1000 to 2000 counts per second.

As a result, the invention can provide an electron microscope that is capable of producing a large quantity of generated X rays without the need for a user to manually adjust the beam current, and without a risk of impairing the performance of the X-ray detector.

(2) The electron microscope according to the invention may further comprise a database having data including X-ray spectra (reference spectra) of a plurality of kinds of standard substances and labels containing names of substances corresponding to the respective reference spectra, and means for performing the steps of:

checking an X-ray spectrum (sample spectrum) of the specimens against the reference spectra in the database;

calculating the degree of matching in spectral shape between the sample spectrum and the reference spectra;

extracting a reference spectrum having the highest degree of matching from the database;

setting up a plurality of X-ray energy regions so as to have sensitivity data for X-ray energy of the X-ray detector, and to include peaks of the sample spectrum when analyzing by identifying substances of the specimens on the basis of the label corresponding to the reference spectrum that is extracted;

standardizing the intensity of the reference spectra into an intensity of the sample spectrum for each of the X-ray energy regions as set up after multiplying the reference spectra by the sensitivity data;

checking the sample spectrum against the reference spectra as standardized and extracting one or a plurality of the reference spectra in descending order of the degree of matching between the sample spectrum and the reference spectra for each of the X-ray energy regions; and outputting a label or labels corresponding to the one or the plurality of the reference spectra, the degree of matching, and a numerical value used in the standardization.

Further, a function of outputting the label, the degree of matching, and the numerical value as described above may include, for example, outputting first to third candidate elements in descending order of the degree of matching. Still further, the electron microscope according to the invention may display an intensity ratio of the sample spectra obtained by electron beam irradiation at not less than two varied acceleration voltages. Furthermore, the sensitivity data may contain an intensity ratio of an X-ray spectrum of a standard specimen, including a silicon wafer, obtained at the time of obtaining the reference spectra, to an X-ray spectrum of the standard specimen, obtained immediately before matching.

Accordingly, it becomes possible to implement analysis of elements as to which spectra are overlapped with each other, and to obtain information on which element is contained in a foreign particle by checking the X-ray spectrum of the foreign particle, as well as a substrate under the foreign particle, in a region different in size, so that an electron microscope that is capable of analyzing elements and substances with high sensitivity and high precision can be provided. Further, since a difference in spectral sensitivity between instruments can be corrected by a correction curve using a standard specimen, it is sufficient to prepare one kind of database, which can be reinforced with a database acquired in another instrument without wasting the latter. Still further, even if the spectral sensitivity of the same instrument undergoes a change due to stains, etc. on the X-ray window, it is possible to effectively maintain matching with a database by acquiring a correction curve by use of a standard specimen.

(3) The electron microscope according to the invention may further comprise a memory for storing a plurality of X-ray spectra (sample spectra) at a plurality of observation points on the specimens, respectively, that have been obtained by the X-ray detector, and means for categorizing the plurality of the sample spectra into one or a plurality of groups of the sample spectra by matching them with each other and performing elemental analysis of one X-ray spectrum selected from the respective groups.

Furthermore, the electron microscope according to the invention may comprise a function of matching the sample spectra with each other for each of one or a plurality of X-ray energy regions set up so as to include respective peaks of the sample spectra.

Further, the electron microscope according to the invention may automatically categorize the plurality of the sample spectra by matching them with each other and perform elemental analysis of the plurality of the sample spectra as categorized.

Thus, it becomes possible to categorize, on the basis of representative spectra, without checking an X-ray spectrum obtained at every foreign particle point against a database every time the X-ray spectrum is obtained, so that the invention can provide an electron microscope that is capable of analyzing the elemental composition of respective foreign particles in a short time by matching the representative spectra only against the database, or performing qualitative analysis or quantitative analysis.

BRIEF DESCRIPTION OF THE DRAWINGS

FIG. 8 is a table showing another display example of output results of elemental analysis, according to the second embodiment of the invention;

FIGS. 21A and 21B are diagrams showing the dependency of X-ray spectra of foreign particles, that have adhered to the surface of a wafer, on the thickness of the foreign particles; and FIG. 22 is a schematic diagram showing sectional views of a specimen for illustrating the difference between an X-ray spectrum of a portion of the specimen having no foreign particle and an X-ray spectrum of a portion of the specimen having a foreign particle.

DETAILED DESCRIPTION OF THE PREFERRED EMBODIMENTS

Embodiments of an electron microscope, including an apparatus for effecting x-ray analysis, and a method of analyzing specimens using the same, according to the invention, will be described hereinafter.

First Embodiment

Figure 1:
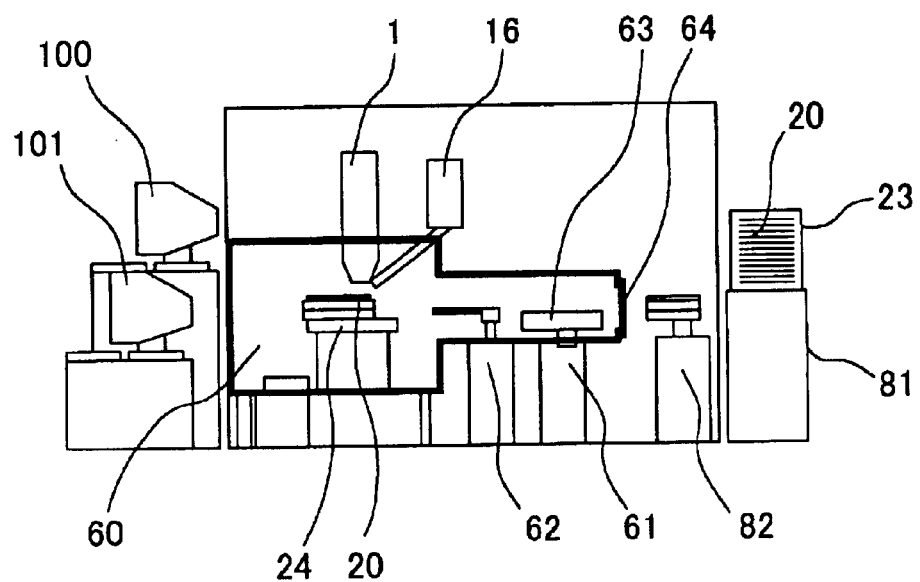
FIG. 1 is a schematic diagram showing a side view of a first embodiment of an instrument according to the invention, illustrating the configuration of the instrument in its entirety.
Figure 2:
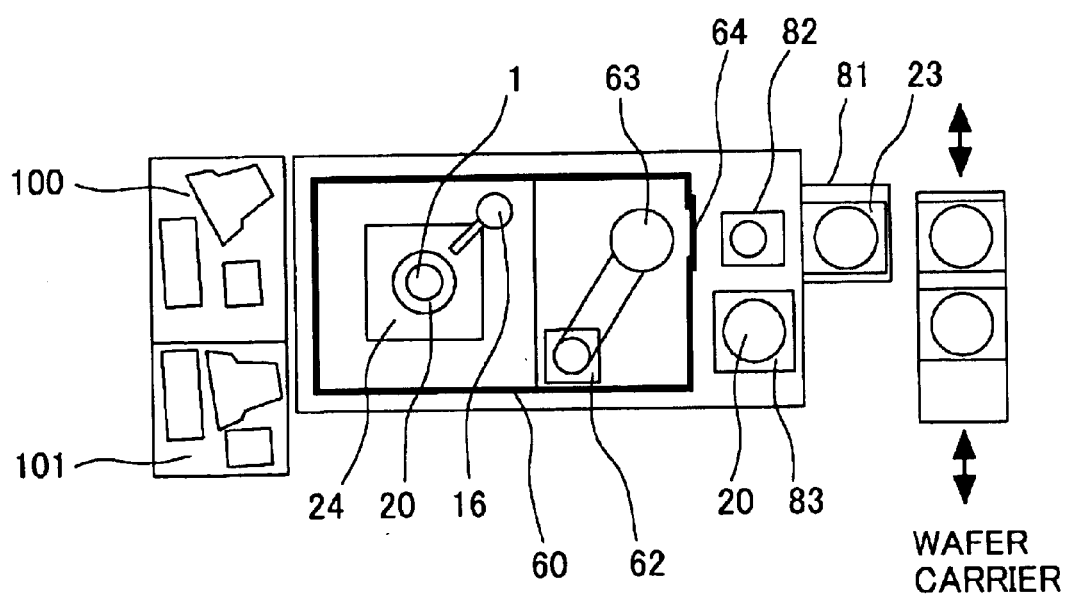
FIG. 2 is a schematic diagram showing a plan view of the first embodiment of the instrument according to the invention, illustrating the configuration of the instrument in its entirety.
Figure 3:
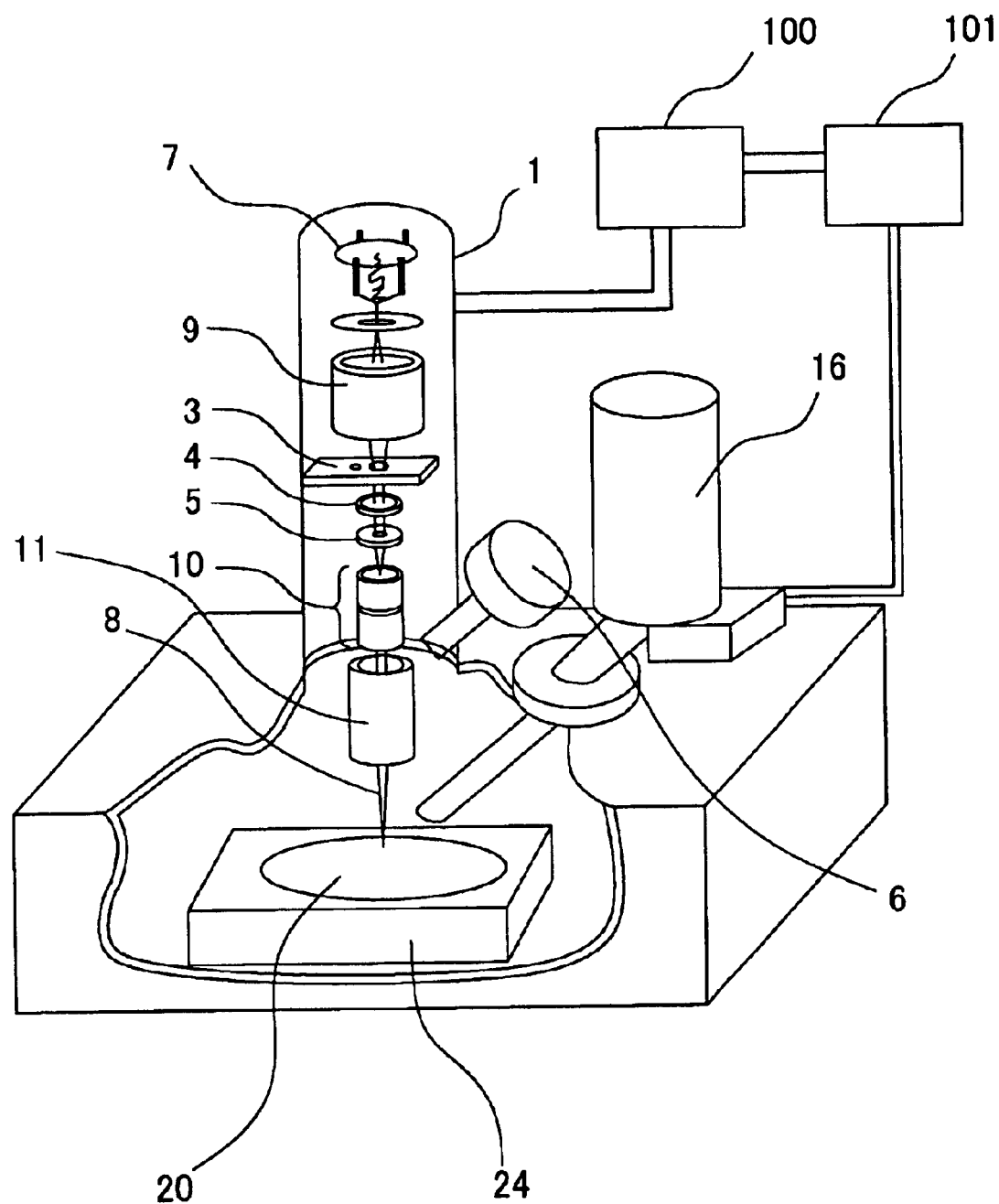
FIG. 3 is a partly sectional perspective view of the instrument according to the first embodiment of the invention.

The instrument configuration and the operation thereof according to a first embodiment of the invention will be described hereinafter with reference to FIGS. 1 through 5. FIGS. 1 and 2 show the configuration of an instrument in its entirety, and FIG. 3 shows in detail the configuration of a scanning electron microscope optical system and the periphery of a specimen stage. With the present embodiment, a portion of the electron microscope according to the invention, that is applicable to a wafer, will be considered. Further, FIG. 3 is a partly sectional perspective view of the instrument shown in FIG. 1, although there exists some difference therebetween in respect of the orientation of the instrument and in the detail for the sake of convenience in description, however, there is, in effect, no difference therebetween.

In FIG. 1, an electron beam optical system 1 and an X-ray detector 16 are suitably disposed in an upper part of a vacuum specimen chamber 60 at the central part of an instrument system. A specimen stage 24, on which a wafer 20 as a specimen is to be placed, is disposed inside the vacuum specimen chamber 60. Two units of the optical system 1 are adjusted such that the respective center axes thereof intersect each other at one point in the vicinity of the surface of the wafer 20. The specimen stage 24 has a built-in mechanism for moving the wafer 20 back and forth and from side to side with high precision, thereby controlling the positioning of the wafer such that a designated spot on the wafer 20 comes directly below the electron beam optical system 1. Further, the specimen stage 24 is capable of rotating, turning upside down, or tilting. The vacuum specimen chamber 60 is connected to an exhaust system (not shown), and it is controlled so as to be at a suitable vacuum. Further, the electron beam optical system 1 is also provided with an individual exhaust system (not shown), thereby maintaining a suitable degree of vacuum. Wafer introduction means 61 and wafer carrying means 62 are provided inside the vacuum specimen chamber 60. A wafer transfer robot 82 and cassette introduction means 81 are disposed so as to be adjacent to the vacuum specimen chamber 60. There are a main controller 100 for controlling and managing a series of processes for the instrument as a whole, and an X-ray detector controller 101, positioned on the left side of the vacuum specimen chamber 60 so as to be adjacent thereto. The main controller 100 and the X-ray detector controller 101 are set up such that data can be mutually exchanged therebetween, and the main controller 100 can control the X-ray detector controller 101.

Now, an operation of wafer introduction, according to the present embodiment, will be broadly described hereinafter. When a wafer cassette 23 is placed on a table of the cassette introduction means 81, and a command for starting the operation is issued from the main controller 100, the wafer transfer robot 82 takes out a wafer 20 as a specimen from a designated slot inside the wafer cassette 23, and orientation adjustment means 83, as shown in FIG. 2, operates to adjust the orientation of the wafer 20 toward a predetermined position. Subsequently, at a point in time when a hatch 64 in the upper part of the wafer introduction means 61 is opened by the wafer transfer robot 82, the wafer 20 is placed on a stage 63. Upon closing the hatch 64, air is exhausted by the vacuum exhaust means (not shown), and, thereafter, the wafer carrying means 62 picks up the wafer 20 on the stage 63 and places the same on the specimen stage 24 inside the vacuum specimen chamber 60. In this connection, the specimen stage 24 is provided, as necessary, with means for chucking the wafer 20 to correct warpage thereof or to prevent vibration thereof.

Next, referring to FIG. 3, the electron beam optical system and X-ray detector will be described. With the electron microscope according to the invention, the electron beam optical system I comprises an electron gun 7, an electron lens 9 for focusing the electron beam 8 emitted from the electron gun 7, an aperture 3 for cutting out unnecessary portions of the electron beam 8, a blanking coil 4, a Faraday cup 5, an electron beam scanning coil 10, and an objective lens 11. The Faraday cup 5 has a through-hole for allowing the electron beam 8 to pass therethrough, and the blanking coil 4 deflects the electron beam 8 from the through-hole of the Faraday cup 5 only when measuring current of the electron beam 8, before causing the electron beam 8 to fall on the Faraday cup 5. Besides the above-described components, there are a secondary electron detector 6 for detecting secondary electrons from the wafer 20, which have been emitted upon irradiation of the electron beam 8 onto the wafer 20, the specimen stage 24 which is movable and on which the wafer 20 is placed, the X-ray detector 16 for detecting X rays radiated from the wafer 20a at the time of the irradiation of the electron beam 8 onto the wafer 20, and a reflection electron detector (not shown) for detecting reflected electrons emitted from a specimen. The electron beam optical system, specimen stage, secondary electron detector, and reflection electron detector are controlled by the main controller 100.

Now, in connection with the present embodiment, a process of evaluation, mainly on the elemental composition after introduction of the wafer 20, will be broadly described.

Upon the electron beam 8 falling on the wafer 20, secondary electrons and reflected electrons, reflecting the surface geometry of the wafer 20, are emitted from the surface of the wafer 20, and, at the same time, X-rays containing characteristic X-rays having energy inherent to the elemental composition of portions of the wafer 20 are produced in the vicinity of electron beam incident regions. By moving the specimen stage 24 such that a desired observation region on the wafer 20 comes directly below the electron beam optical system 1, the electron beam 8 is caused to scan the surface of the observation region using a deflection lens, and foreign particles on the wafer 20 are observed on the basis of secondary electron images and reflection electron images that are obtained by detecting the secondary electrons and reflected electrons emitted from the wafer 20, adjustment being made such that the foreign particles are positioned at the center of the observation region. Subsequently, X rays produced by irradiation of the foreign particles, while the electron beam 8 is kept in a stationary state, are detected by the X-ray detector 16, thereby obtaining an X-ray spectrum. Thereafter, by analyzing the X-ray spectrum, the elemental composition of the foreign particles is found. The X-ray spectrum and results of analysis are shown on a display device of the main controller 100 and are stored in a memory at the same time. On the basis of the coordinates of a position of each of the foreign particles on the wafer 20, obtained by an optical foreign particle inspection apparatus, the specimen stage can be controlled such that the foreign particles enter the observation region.

Figure 19:
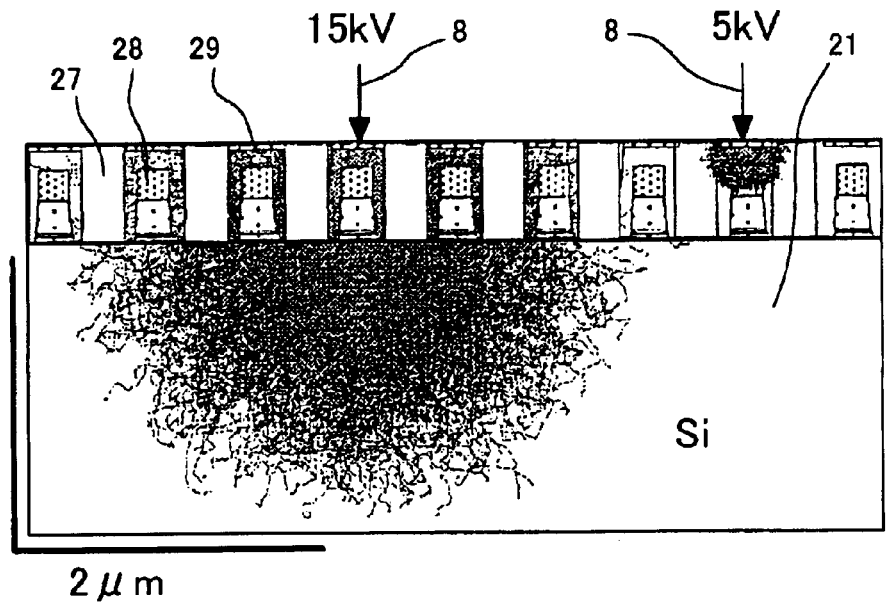
FIG. 19 is a diagram showing the relationship in position between electron beam scattering regions inside a specimen and a typical semiconductor.

As shown in FIGS. 18 and 19, the acceleration voltage of the electron beam 8 is characterized in that the lower the acceleration voltage is, the smaller the scattering region of the electron beam 8 inside the wafer 20 becomes. When observing the foreign particles on the wafer 20, electrons penetrating through the foreign particles scatter inside the wafer 20, so that a substance, existing in the vicinity of regions underneath the foreign particles, is mixed as a background noise into the X-ray spectrum as observed. From the viewpoint described above, it can be said that the lower the acceleration voltage is, the more convenient it is from a point of elemental analysis of the foreign particles. This is effective particularly when body structures composed of several elements are formed in the vicinity of the surface of the wafer 20. On the other hand, if the acceleration voltage is lowered, the characteristic X-rays that can be excited are restricted, so that the elements that can be analyzed are also restricted. Accordingly, in the case where semiconductor elements of submicron size are being formed, the acceleration voltage at several kilovolts (kV) is adopted.

A high count-number of an X-ray spectrum with high-energy resolving power is necessary for elemental analysis with high precision. With the X-ray detector according to the present embodiment, use is made of a cooled silicon semiconductor detection element; and, in order to take measurements without impairing energy resolving power and efficiency, that is, with minimum omission in counting, it is preferable to cause X rays ranging from 1000 to 2000 in number to fall on the specimen per second. The count-number of X rays per second is called an X-ray count rate, and cps (counts per second) is generally used as units thereof. With the present embodiment of the invention, the X-ray count rate can be measured using the X-ray detector controller.

In the case where electron beams of an identical current strength are irradiated onto a silicon wafer with the acceleration voltage at 15 kV and 5 kV, respectively, the X-ray count rate in the case of 15 kV is about ten times as large as that in the case of 5 kV. Accordingly, in order to perform observation with a high X-ray count rate, there is a need for adjusting the current quantity so as to correspond to an acceleration voltage.

Figure 4:
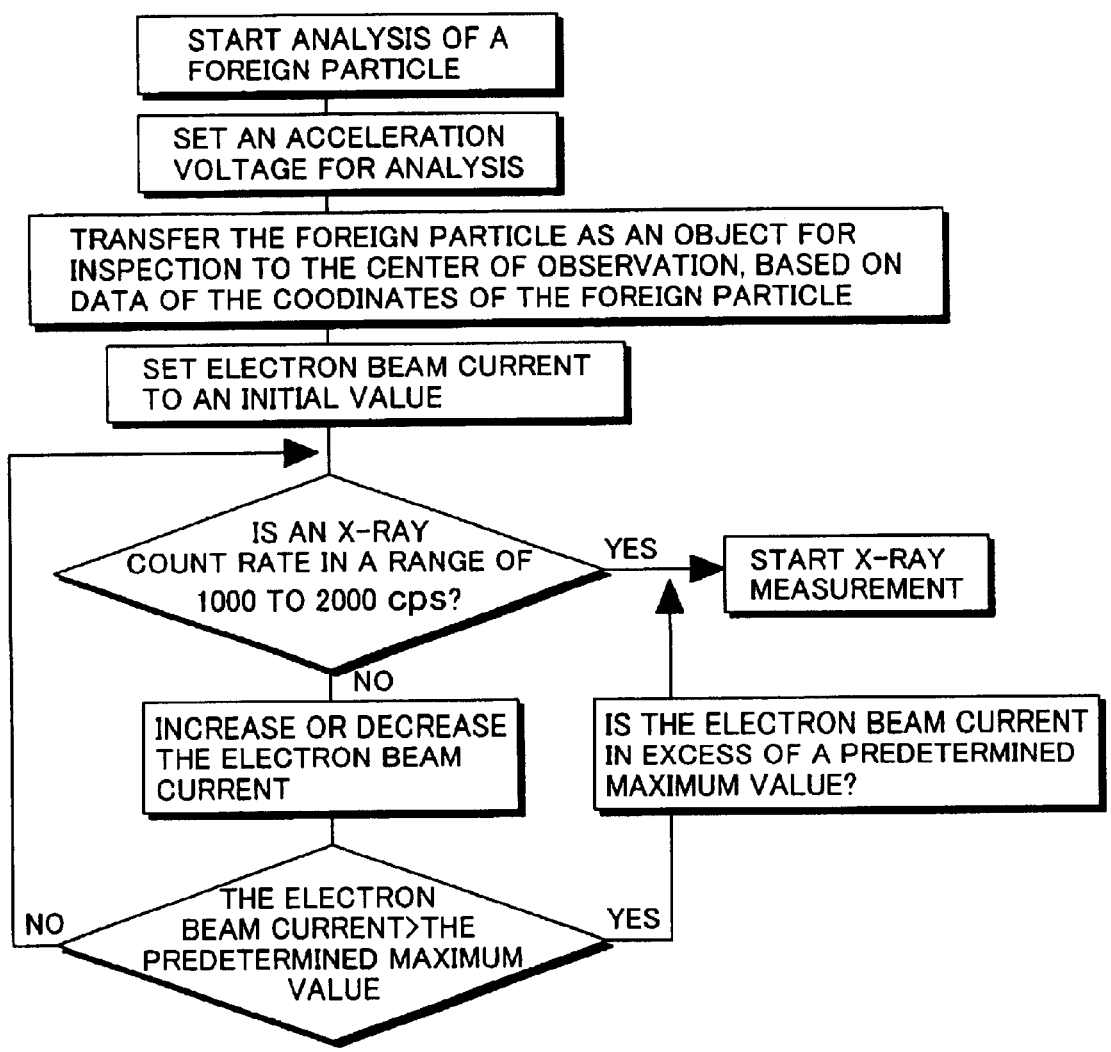
FIG. 4 is a flow chart showing a method of automatically setting electron beam irradiation conditions according to the first embodiment of the invention.

FIG. 4 is a flow chart showing the setting of an operation condition of the electron beam optical system. With the present embodiment of the invention, as shown in FIG. 4, after setting an acceleration voltage at first, an initial value of current strength is set to, for example, 100 pA, the wafer 20 is irradiated, and the main controller 100 receives an X-ray count rate from the X-ray detector controller 101. The main controller 100 increases or decreases the current strength of the electron beam 8 so as to correspond to the X-ray count rate. As a result of such an operation, the X-ray count rate is set to an optimum value for detection of X rays, in a range of 1000 to 2000 cps. However, since the maximum value of electron beam current is dependent on the instrument in use, the beam current is set to the maximum value of the instrument in case a set value as described above comes to exceed the maximum value.

Figure 5:
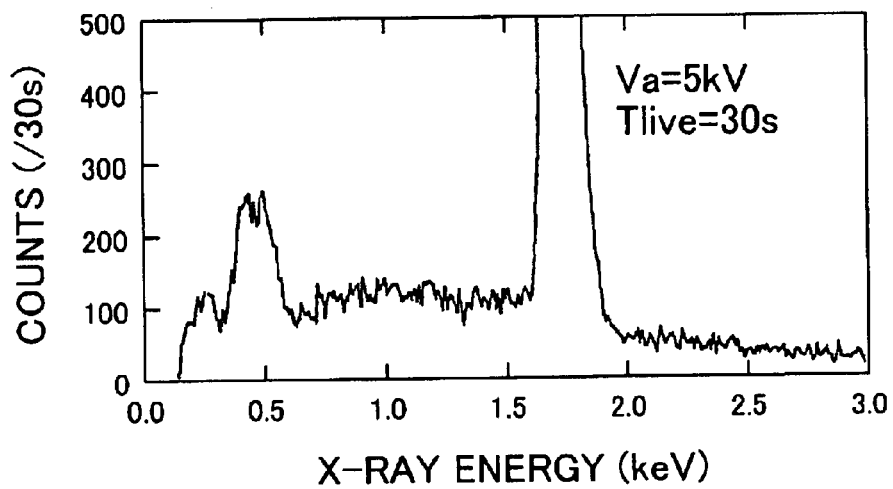
FIG. 5 is a graph showing an example of an X-ray spectrum obtained according to the first embodiment of the invention.
Figure 20:
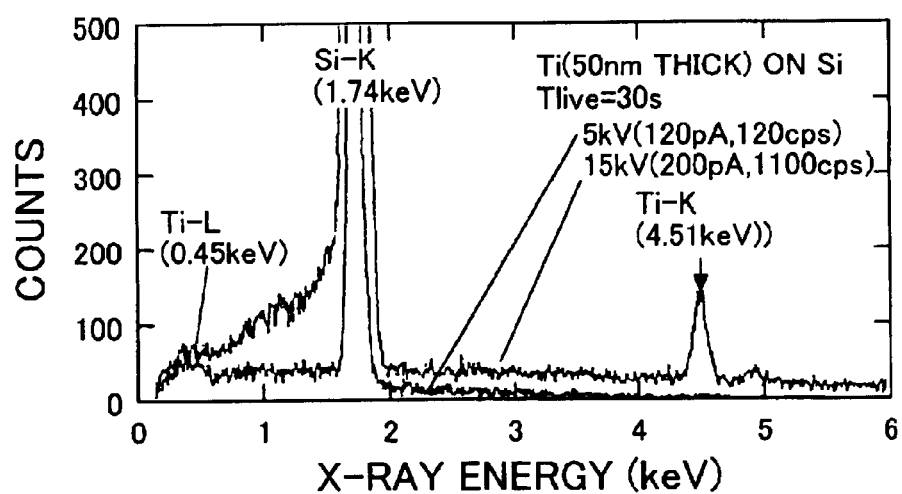
FIG. 20 is a graph showing comparison of X-ray spectra obtained at varied acceleration voltages.

FIG. 5 is a profile showing an X-ray spectrum of a foreign particle of titanium (Ti), 50 nm thick, present on the surface of a silicon wafer, obtained as a result of setting the operation condition of the electron beam optical system, as described above. The height (count-number from a background X-ray signal level) of a Ti-L line peak appearing at 0.45 keV of X-ray energy becomes about 150 counts, which is higher by about one order of magnitude during an equivalent measuring time, as compared with the X-ray spectrum of the foreign particle of titanium (Ti), that is obtained with the acceleration voltage at 5 kV, as shown in FIG. 20, thereby obtaining a peak height sufficient for analysis, so that elemental analysis with a high S/N ratio can be attained. Hence, observation with a high resolving power and high precision becomes possible.

Second Embodiment

Figure 6:
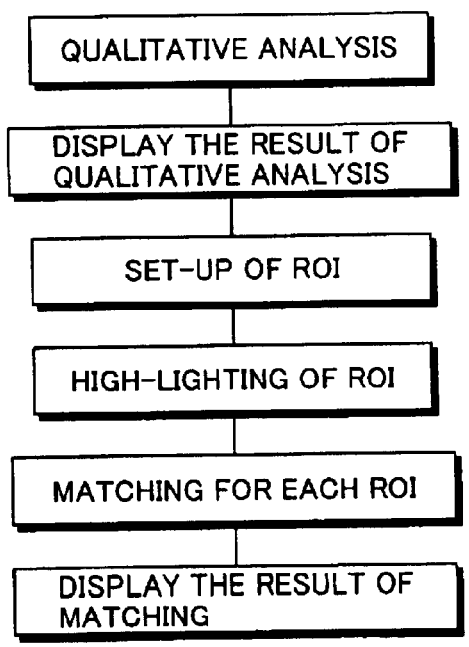
FIG. 6 is a flow chart showing a method of matching X-ray spectra according to a second embodiment of the invention.
Figure 7:
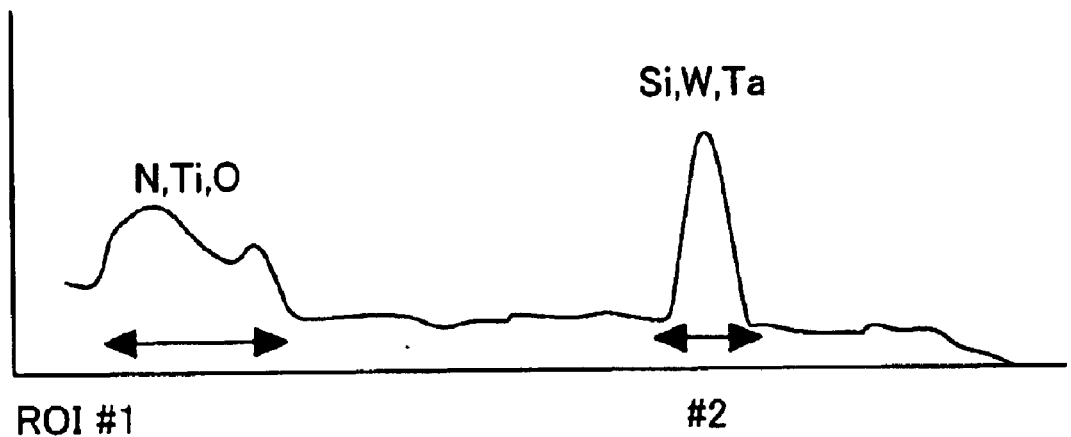
FIG. 7 is a graph showing a display example of output results of elemental analysis, according to the second embodiment of the invention.

A second embodiment of an electron microscope including an apparatus for x-ray analysis, and a method of analyzing specimens using the same, according to the invention, will be described hereinafter with reference to FIG. 3 and FIGS. 6 through 8. FIG. 6 is a flow chart showing a method of analyzing X-ray spectra. FIGS. 7 and 8 are views showing an X-ray spectrum and output results of analysis, as produced on a display device of a main controller, respectively.

An X-ray detector controller 101 according to the present embodiment, which is the same in configuration as that shown in FIG. 3, has a qualitative analysis function of presuming a candidate element on the basis of an X-ray energy value corresponding to a peak of an X-ray spectrum, and other functions, as will be described hereinafter. Further, the X-ray detector controller 101 has a memory; and, a database containing a plurality of X-ray spectra (reference spectra), against which an X-ray spectrum as obtained is checked, is stored in the memory. Individual reference spectra are designated by specimen names corresponding thereto, respectively. The reference spectra are prepared for substances used in manufacturing semiconductor elements, such as silicon, oxygen, copper, tungsten, gold, titanium, tantalum, titanium nitride TiN, tantalum nitride TaN, silicon dioxide SiO2, and so forth. Furthermore, a main controller 100 is capable of exchanging information with the X-ray detector controller 101, and it has functions of controlling the X-ray detector controller 101, receiving necessary information from the X-ray detector controller 101 to thereby show the information on a display device of the main controller 100, and storing the information in the memory.

In accordance with the flow chart shown in FIG. 6, the method of analyzing the specimens will be described hereinafter. First, qualitative analysis is performed on an X-ray spectrum of a foreign particle, obtained as described in the first embodiment, and the X-ray spectrum and results of the qualitative analysis are shown on the display device, as shown in FIG. 7. In FIG. 7, element names displayed above respective peaks of the X-ray spectrum represent the results of the qualitative analysis. Next, a region for use in checking the X-ray spectrum against the database is set up. The region for use in checking is referred to an ROI (region of interest). With the present embodiment, a plurality of the ROIs are set up so as to include a portion of the base, corresponding to the respective peaks of the X-ray spectrum, as shown in FIG. 7. The ROIs are set up by a method of deeming portions of the X-ray spectrum, on the upper side of the background, that is, on the plus side thereof, as the ROIs. After setting up the ROIs, the ROIs and numbers corresponding thereto are displayed by double-headed arrows (highlighting of the ROIs). In the case where peaks of the X-ray spectrum are overlapped with each other, as with the case of an ROI indicated by #1 in FIG. 7, this is deemed as one ROI. Subsequently, for each of the ROIs that are set up, the X-ray spectrum is checked against X-ray spectra in the database stored in the memory of the X-ray detector controller 101 (matching). FIG. 8 shows results of matching, displaying three lists in descending order of matching scope and degree of matching for each of the ROIs. The degree of matching is evaluated by X2, which is represented by the following expression:

$$x^2 = \sum_{i=m1}^{m2} (aT_i - L_i)^2 / L_i \qquad \text{expression (1)}$$

where Ti, Li represent the value of the X-ray spectrum to be checked, and respective values of the X-ray spectra in the database, respectively, m1, m2 are energy values at a start point and an end point, of the respective ROIs, respectively, and a is parameter for use in aligning the height of a peak in the respective ROIs with that of the reference spectra to be checked against. In case there exist a plurality of peaks within each of the ROIs, the highest peak is used for matching. On the presumption that the smaller the value of $X^2$, the better the degree of matching is, there are displayed results showing $X^2$, a, respective labels of the reference spectra in descending order of the degree of matching. With the present embodiment, matching is performed for the full range of acquired energy besides the ROIs as set up, outputting results of such matching as shown in the bottom row of the table in FIG. 8. This is effective for analysis of very thick foreign particles.

In FIG. 8, columns denoted by best, second, and third, respectively, indicate the descending order of the degree of matching. The X-ray spectrum obtained is shown to have best matched with the reference spectrum with a label designated as TiN (titanium nitride). In the column of energy regions, start values and end values are shown in units of keV, respectively. It becomes possible to obtain information concerning an element or thickness of a substance, corresponding to the parameter a, on the basis of the parameter a.

The main controller 100 stores the information shown in the table in FIG. 8 together with secondary electron images, reflection electron images, and position information, in the memory, and it displays the elemental distribution of the foreign particles on a wafer on the basis of the position information and the information shown in the table in FIG. 8. Furthermore, the main controller 100 provides a user with presumed results concerning causes for generation of the foreign particles by checking against a database showing a relationship with the processing steps.

As described in the foregoing, with the present embodiment, since the X-ray spectrum as obtained is checked against the X-ray reference spectra in the database for each of the ROIs, it becomes possible to avoid a problem that respective X-ray spectra of foreign particles come to significantly differ from each other depending on the size (thickness) thereof, even if the foreign particles are the same in elemental composition, resulting in failure to match with any of the X-ray reference spectra stored in the database. This will eliminate the need for preparing X-ray reference spectra for foreign particles with varied thickness, so that the number of X-ray reference spectra to be checked against can be reduced, thereby enabling matching to be executed with a high throughput.

In the case where X-ray detection of a foreign particle of tungsten is performed by an electron beam with the acceleration voltage at 5 kV, the characteristic X-ray peak attributable to tungsten comes to be overlapped with the characteristic X-ray peak attributable to silicon or tantalum (Ta), so that it is difficult to discriminate therebetween by merely observing the X-ray spectra thereof. However, with the use of this method, it has since become possible to discriminate therebetween with high precision. With the present embodiment, in executing matching for each of the ROIs, there are displayed matching results of up to three cases in descending order of degree of matching; however, there may be displayed instead matching results of cases where X2 as an indicator of the degree of matching is not greater than a predetermined value. Further, the ROIs are set up automatically, however, a method of a user setting up the ROIs by inputting the same may be used in combination with the foregoing method. Furthermore, X2 represented by the expression (1) is adopted as the indicator of the degree of matching; however, it is to be pointed out that the advantageous effects of the invention are not impaired by use of another method of adopting the sum of the square of remainder between both the X-ray spectra, and so forth, as an indicator of the degree of matching.

Third Embodiment

A third embodiment of the invention will be described hereinafter with reference to FIG. 9. With the present embodiment, the configuration of the instrument is the same as that described in connection with the first and second embodiments, respectively, but the method of analyzing specimens differs from that for the first embodiment and the second embodiment, respectively.

Figure 9:
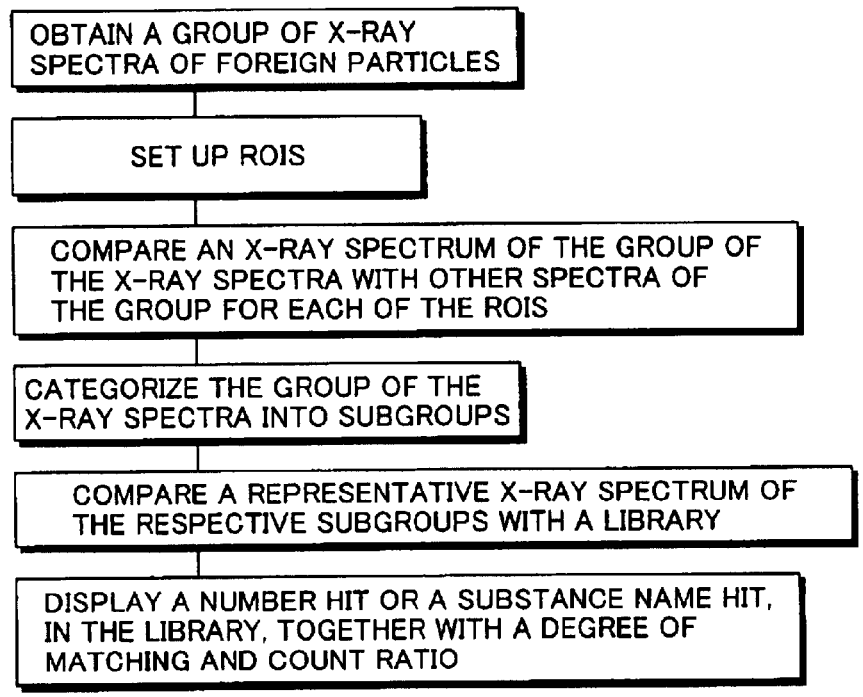
FIG. 9 is a flow chart showing a method of performing elemental analysis according to a third embodiment of the invention.

As shown in FIG. 9, with the present embodiment, firstly, X-ray spectra of a plurality of foreign particles to be evaluated are obtained beforehand, and the spectra data are stored in a designated region of the memory provided in the X-ray detector controller 101 shown in FIG. 3 (a group of X-ray spectra of foreign particles). Respective X-ray spectra are provided with labels corresponding to respective coordinates of positions of the foreign particles, and they are stored so as to be able to identify which of the X-ray spectra corresponds to a foreign particle located at which position.

Subsequently, ROIs are set up for a specific X-ray spectrum of the group of the X-ray spectra of the foreign particles, as with the case of the second embodiment, and by checking the specific X-ray spectrum against other X-ray spectra of the group of the X-ray spectra of the foreign particles, the group of the X-ray spectra of the foreign particles is categorized into subgroups of the X-ray spectra having a high degree of matching with each other. Next, one X-ray spectrum is selected from one of the subgroups of the X-ray spectra, as categorized, and it is checked against the X-ray reference spectra in the database in accordance with the procedure described in connection with the second embodiment, thereby identifying an element and a substance on the basis of an X-ray reference spectrum matching the respective subgroups.

With the present embodiment, instead of checking the respective X-ray spectra of all of the foreign particles for inspection against X-ray reference spectra, the X-ray spectra of the foreign particles are categorized into subgroups of the X-ray spectra beforehand, and one X-ray spectrum selected from the respective subgroups is checked against the X-ray reference spectra, thereby identifying an element and a substance. Accordingly, operation on the whole can be implemented with high throughput. This method is effective particularly in the case where foreign particles on a wafer, as the objects for inspection, are generated due to a certain cause and are composed of substantially an identical substance.

Figure 15:
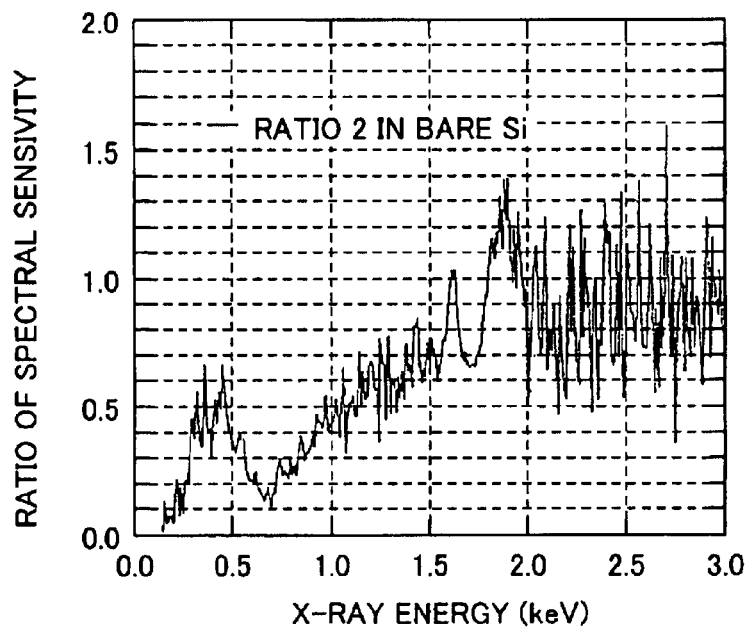
FIG. 15 is a graph showing an example of a ratio of spectral sensitivity for use in matching of spectra according to the embodiments of the invention.

With the first through third embodiments, as described above, if the spectral sensitivity of the X-ray detector varies when checking an X-ray spectrum obtained against the X-ray reference spectra in the database, the matching precision deteriorates. The spectral sensitivity undergoes variation due to variation with respect to an X-ray detection element of the X-ray detector controller and an X-ray transmission window of the X-ray detector, the mounting position of the X-ray detector relative to the electron microscope (the distance from a specimen to the X-ray detection element, and the X-ray takeout angle), the deterioration of transmittance caused by contamination of the X-ray transmission window after mounting, and so forth. FIG. 15 shows a ratio of spectral sensitivity with reference to an X-ray spectrum from the same silicon specimen, that is obtained by another electron microscope with a different X-ray detector mounted thereon.

With the embodiments of the invention, the ratio of spectral sensitivity in the database to the spectral sensitivity at the time of measurement, as shown in FIG. 15, is obtained beforehand, and matching is performed with the ratio of spectral sensitivity described being taken into consideration in order to prevent deterioration in matching precision, due to variation in spectral sensitivity. In addition, since there can be a possibility of the spectral sensitivity undergoing a change due to contamination of the X-ray transmission window and replacement of the X-ray detector, it is preferable to periodically measure a new ratio of spectral sensitivity.

By so doing, the need for preparing a database for every instrument is eliminated, so that it becomes possible to make effective use of the database.

Furthermore, by copying a file for X-ray spectra, the same can be added to the database with ease.

Fourth Embodiment

A fourth embodiment of the invention will be described hereinafter with reference to FIG. 5 and FIGS. 10 through 14. The present embodiment provides an example of a method of analyzing the elemental composition of a foreign particle with high precision by electron beam irradiation at varied acceleration voltages.

Figure 10:
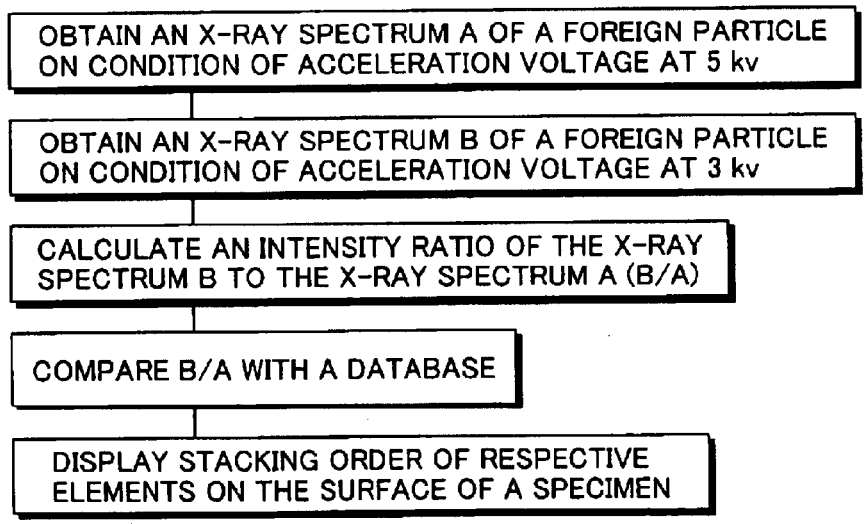
FIG. 10 is a flow chart showing a method of performing elemental analysis according to a fourth embodiment of the invention.
Figure 11:
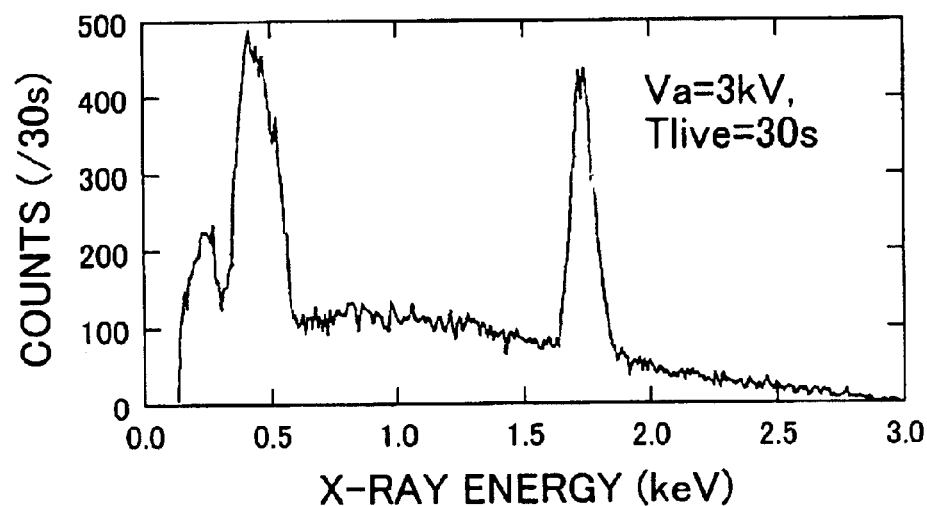
FIG. 11 is a graph showing an example of an X-ray spectrum obtained according to the fourth embodiment of the invention.

With the present embodiment, as shown in the flow chart of FIG. 10, firstly, by electron beam irradiation with an acceleration voltage at 5 kV, an X-ray spectrum of a foreign particle on a wafer is obtained and is designated as A to be stored in a memory provided in an X-ray detector controller. Subsequently, by electron beam irradiation with acceleration voltage at 3 kV, an X-ray spectrum of the same foreign particle is obtained and is designated as B to be similarly stored in a memory.

Thereafter, an intensity ratio of the spectrum B to the spectrum A (B/A) is calculated, and by comparing B/A with a database, there are displayed results of a determination on which element corresponds to the element of the foreign particle, and which element corresponds to the element of a substrate.

Figure 13:
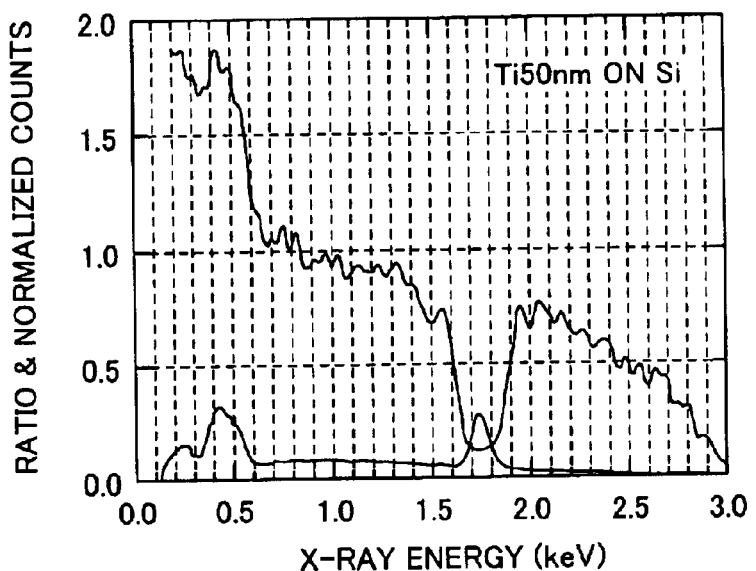
FIG. 13 is a graph showing an example of an intensity ratio between X-ray spectra according to the fourth embodiment of the invention.
Figure 14:
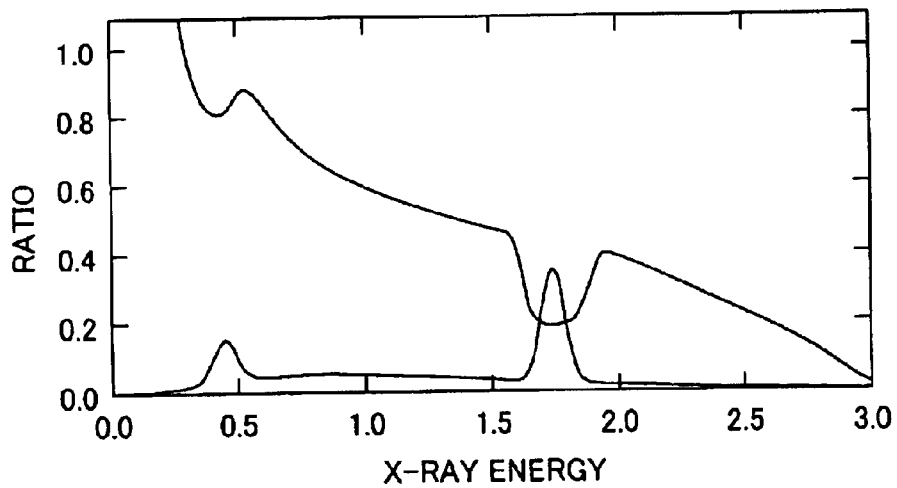
FIG. 14 is a graph showing an example of an intensity ratio between reference spectra according to the fourth embodiment of the invention.

An example is described hereinafter. FIGS. 5 and 10 show an X-ray spectrum obtained by irradiating a foreign particle on a wafer with an electron beam with an acceleration voltage at 5 kV and 3 kV, respectively. With either of the X-ray spectra, three characteristic peaks are observed, and they are identified as carbon, titanium, and silicon, respectively, in ascending order of energy intensity. FIG. 13 shows an intensity ratio of the X-ray spectrum shown in FIG. 5 to that shown in FIG. 11. For reference, the X-ray spectrum corresponding to the electron beam irradiated with an acceleration voltage at 3 kV is shown by a graph in the lower part in the figure. The vertical axis is adjusted for easy viewing, and the horizontal axis indicates X-ray energy intensity. FIG. 14 shows an intensity ratio of an X-ray spectrum of a compound composed of uniformly distributed titanium and silicon against an electron beam irradiated with an acceleration voltage at 5 kV to the same at 3 kV. The X-ray spectrum shown in the lower part in the figure is one corresponding to the electron beam irradiated with an acceleration voltage at 3 kV. It can be seen by comparing FIG. 13 with FIG. 14 that a titanium peak at 0.45 keV of X-ray energy differs in trend from a silicon peak at 1.75 keV of X-ray energy. More specifically, in a part (background X-ray) of FIG. 13, as well as in FIG. 14, having no peak, the curve is shown to fall downward toward the right, and in the case of a specimen of the compound composed of uniformly distributed titanium and silicon (FIG. 14), the curve has a downward dent at points thereof, corresponding to the respective intensity ratios at the peaks of titanium and silicon, respectively. In contrast, in the case of the foreign particle (titanium) on the wafer (FIG. 13), the curve has an upward bulge at a point thereof, corresponding to the intensity ratio at the peak of titanium, while the curve has a downward dent at a point thereof corresponding to the intensity ratio at the peak of silicon. Furthermore, the downward dent in FIG. 13 is shown to be an even deeper dent in comparison with that in the case of the specimen of the compound composed of uniformly distributed titanium and silicon. On the basis of the above finding, there are displayed results of a determination that titanium is the element of the foreign particle, and silicon is a substance disposed underneath the foreign particle.

Figures 12A, 12B:
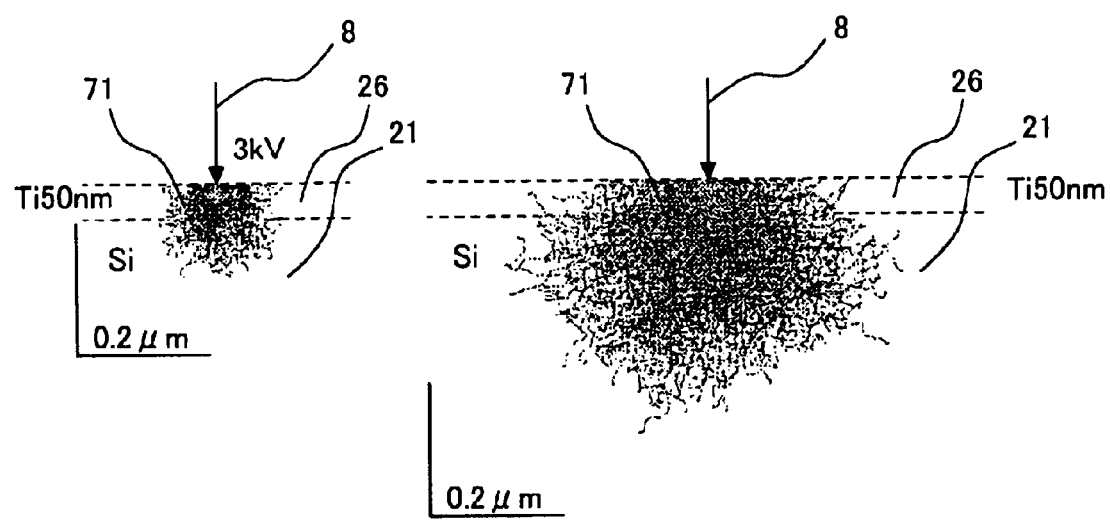
FIGS. 12A and 12B are diagrams showing the principle of operation according to the fourth embodiment of the invention.

FIGS. 12A and 12B show scattering conditions of electrons inside a specimen of a titanium thin film that is 50 nm thick, attached to the top of a silicon substrate, as calculated by a Monte Carlo method. FIG. 12A shows a calculation result in the case of electron beam irradiation at 3 kV of acceleration voltage, and FIG. 12B shows a calculation result in the case of electron beam irradiation at 5 kV of acceleration voltage. A proportion of electrons penetrating through the titanium thin film to be scattered inside the silicon substrate in the case of the acceleration voltage at 3 kV is higher that that in the case of the acceleration voltage at 5 kV. Accordingly, X-rays produced by the electron beam irradiation at 3 kV of the acceleration voltage represent more X-rays emitted from the substance in the vicinity of the surface, that is, titanium, than those emitted from the substrate, that is, silicon. The above-described results of the determination based on the difference in graphs between FIGS. 13 and 14 are derived by taking advantage of such a phenomenon as described. That is, with the present embodiment, it becomes possible to provide information concerning an elemental distribution from an intensity ratio between X-ray spectra as observed, so that a cause of generation of a foreign particle can be searched for with greater accuracy.

Figures 16A, 16B, 16C:
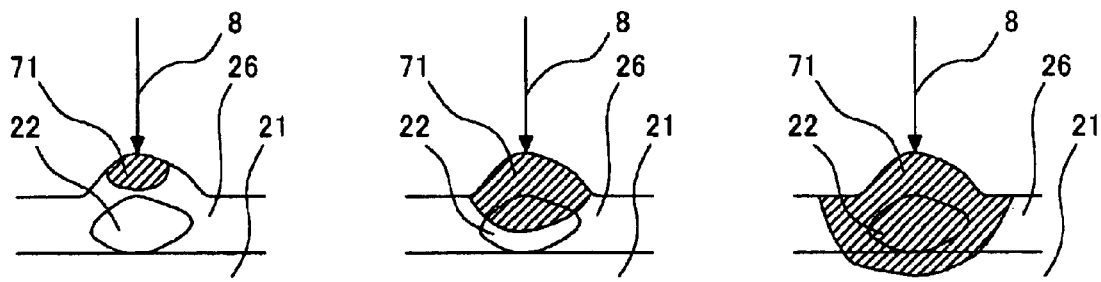
FIGS. 16A through 16C are schematic diagrams illustrating the principle on which a variation of the fourth embodiment is based.
Figure 17A:
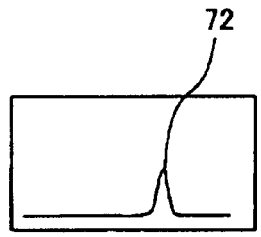
FIGS. 17A through 17C are schematic diagrams of X-ray spectra according to the variation of the fourth embodiment.
Figure 17B:
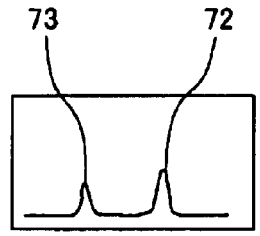
Figure 17C:
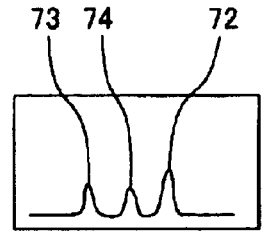
Figure 18A:
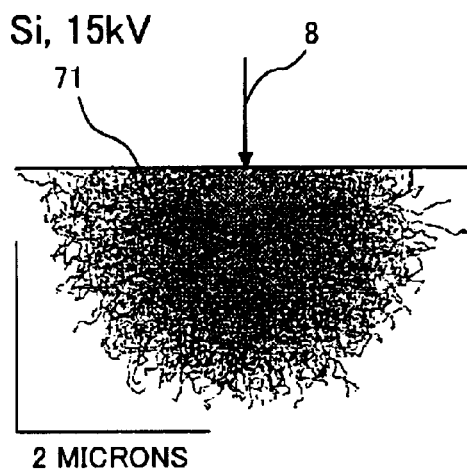
FIGS. 18A through 18D are schematic diagrams showing sectional views of the dependency of electron beam scattering inside specimens on atomic numbers and acceleration voltages.
Figure 18B:
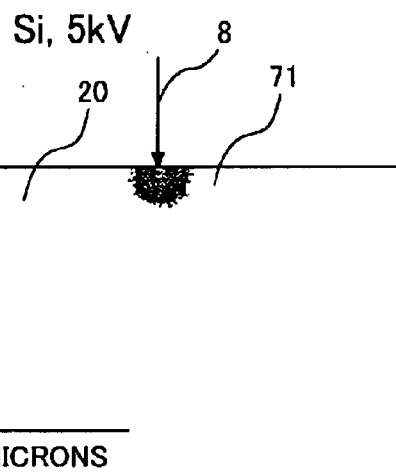
Figure 18C:
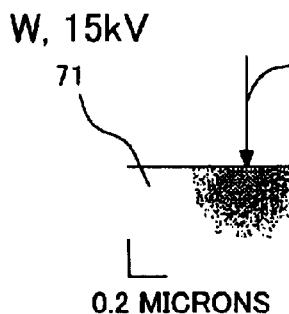
Figure 18D:
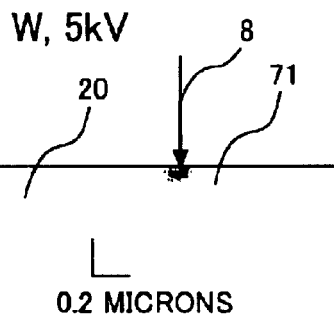

The present embodiment provides method of identifying elements of a foreign particle with X-ray spectra emitted by electron beam irradiation at two varied acceleration voltages. Now, referring to FIGS. 16A to 16C, and 17A to 17C, another method of identifying elements of a foreign particle by use of three varied acceleration voltages will be described. FIGS. 16A through 16C are schematic representations illustrating the principle on which this method is based, and FIGS. 17A through 17C are schematic diagrams of X-ray spectra. As shown in FIGS. 16A through 16C, this method is not directed to a process step which serves as an object for inspection, but for analysis of a foreign particle, called a foreign particle abnormal in shape, that was generated due to a foreign particle 22 appearing immediately before the process step. In FIGS. 16A through 16C, reference numeral 21 denotes a substrate as it appears after a step proceeding the process step which serves as the object for the inspection, and 26 denotes a film formed in the process step and which serves as the object for the inspection. FIG. 16C is a sectional view showing a portion that is abnormal in shape due to the presence of the foreign particle 22 formed immediately before the process step which serves as the object for inspection.

First, as show, in FIG. 16A, the portion that is abnormal in shape is irradiated with an electron beam 8 at an acceleration voltage selected so that the beam 8 does not pass through the film 26, whereupon the electron beam 8 scatters in an electron scattering region 71, and only a characteristic X-ray peak 72 of the element of the film 26 is observed, as shown in FIG. 17A. FIG. 16B shows a case of irradiation with an electron beam 8 having an acceleration voltage higher than that for the electron beam 8 in FIG. 16A. With the acceleration voltage getting higher, the electron beam scatters inside the foreign particle 22, as shown by an electron scattering region 71. In this case, as shown in FIG. 17B, besides the characteristic X-ray peak corresponding to the element of the film 26, a characteristic X-ray peak 73 corresponding to the element of the foreign particle 22 is observed. Next, as shown in FIG. 16C, an electron beam 8 having a still higher acceleration voltage is irradiated, whereupon the electron beam 8 comes to scatter inside the substrate 21 in the step proceeding the process step for the inspection, as indicated in the figure, so that a characteristic X-ray peak 74 corresponding to the element of the substrate 21 is observed, as seen in FIG. 17C. Thus, with this method, it becomes possible to obtain information concerning the element of the foreign particle 22.

The invention has advantageous effects as follows. That is, with the above described embodiments of the invention, it becomes possible to observe foreign particles on the surface of a specimen by electron beam irradiation on condition that the X-ray spectra from the foreign particles can be detected with a high resolving power and a high efficiency, while high precision matching with reference spectra can be implemented and effective analysis can be performed even with a few reference spectra, even in a case where problems occur at the time of X-ray analysis by excitation with an electron beam at low acceleration voltages, which is considered effective for observation of elements of the foreign particles as objects of inspection with a high space resolving power, that is, in the case where characteristic X-rays that can be excited are restricted, peaks of the characteristic X-ray that can be excited are overlapped with each other, and the X-ray spectra of the foreign particles are mixed with the X-ray spectrum of a substrate underneath the foreign particles. Furthermore, it is also possible to obtain information concerning distribution of observed elements inside the specimen. Thus, elemental analysis with high precision and high sensitivity can be performed, and it becomes possible to provide an electron microscope, including an apparatus for x-ray analysis, that is capable of performing inspection of foreign particles for enhancement of the yields in manufacturing LSI devices and so forth, attaining further miniaturization, with high precision, and high space resolving power, and a method of analyzing specimens using the same.

What is claimed is:

1. An electron microscope having an electron beam optical system provided with an electron source and a lens for focusing an electron beam, an optical system controller for controlling the electron beam optical system, a specimen stage on which a specimen is to be placed, an electron detector for detecting electrons emitted from the specimen by irradiating the specimen with the electron beam, an X-ray detector for detecting X rays radiated from the specimen, and a processor for processing signals from both the detectors, and performing image formation and elemental analysis of the specimens, said electron microscope comprising:

means for detecting the count-number of X rays per unit time by detecting the X rays with the X-ray detector; and feedback-controlling a current quantity of the electron beam on the basis of the count-number of X rays per unit time.

2. An electron microscope according to claim 1, wherein the current quality of the electron beam is feedback-controlled such that the count-number of X rays from the specimens falls within a range of 1000 to 2000 counts per second.

* * * * *